(12) United States Patent
Schwartz et al.

(10) Patent No.: US 8,336,541 B2
(45) Date of Patent: Dec. 25, 2012

(54) ENDOTRACHEAL INTUBATION DEVICE

(75) Inventors: John Schwartz, Williamston, MI (US);
Richard Schwartz, Evans, GA (US);
Christopher L. Hogg, Holland, MI (US)

(73) Assignee: AI Medical Devices, Inc., Williamston, MI (US)

( * ) Notice: Subject to any disclaimer, the term of this patent is extended or adjusted under 35 U.S.C. 154(b) by 616 days.

(21) Appl. No.: 12/592,406

(22) Filed: Nov. 24, 2009

(65) Prior Publication Data

US 2011/0120458 A1 May 26, 2011

(51) Int. Cl.
*A61M 11/00* (2006.01)

(52) U.S. Cl. ......... 128/200.26; 128/207.14; 128/207.15; 128/207.16

(58) Field of Classification Search ........ 128/207.14–207.17, 200.26; 600/120, 600/143, 146, 149, 106, 112; 606/205
See application file for complete search history.

(56) References Cited

U.S. PATENT DOCUMENTS

| | | | |
|---|---|---|---|
| 1,720,472 A | 7/1929 | Gagnon | |
| 2,975,785 A | 3/1961 | Sheldon | |
| 3,162,214 A | 12/1964 | Bazinet | |
| 4,236,509 A | 12/1980 | Takahashi et al. | |
| 4,553,005 A | 11/1985 | Glenn | |
| 4,669,172 A | 6/1987 | Petruzzi | |
| 4,846,153 A | 7/1989 | Berci | |
| 4,905,666 A | 3/1990 | Fukuda | |
| 4,911,148 A * | 3/1990 | Sosnowski et al. | 600/136 |
| 4,949,716 A | 8/1990 | Chenoweth | |
| 5,058,577 A | 10/1991 | Six | |
| 5,409,453 A | 4/1995 | Lundquist et al. | |
| 5,441,483 A * | 8/1995 | Avitall | 604/95.05 |
| 5,520,222 A | 5/1996 | Chikama | |
| 5,849,011 A | 12/1998 | Jones et al. | |
| 5,976,075 A | 11/1999 | Beane et al. | |
| 6,321,749 B1 * | 11/2001 | Toti et al. | 128/207.14 |
| 6,432,043 B2 * | 8/2002 | Nakaichi et al. | 600/120 |
| 6,539,942 B2 | 4/2003 | Schwartz et al. | |
| 7,322,357 B2 | 1/2008 | Nelson | |
| 7,458,375 B2 | 12/2008 | Schwartz et al. | |
| 2006/0004258 A1 | 1/2006 | Sun et al. | |
| 2007/0162095 A1 | 7/2007 | Kimmel et al. | |

FOREIGN PATENT DOCUMENTS

JP 5329095 12/1999

OTHER PUBLICATIONS

International Search Report and the Written Opinion of the International Searching Authority dated Nov. 17, 2010, for Application No. PCT/US10/02988.
Form PCT/IB/326 Notification Concerning Transmittal of International Preliminary Report on Patentability (Chapter 1 of the Patent Cooperation Treaty).

* cited by examiner

*Primary Examiner* — Steven Douglas
(74) *Attorney, Agent, or Firm* — Butzel Long

(57) ABSTRACT

An endotracheal intubation device 10 is disclosed. The endotracheal intubation device 10 includes a stylet 100, an elongate rod 300 mounted within the stylet 100 and adapted to deform/curve the stylet 100 as well as an endotracheal tube 400 mounted thereto by contacting an inner wall of the endotracheal tube 400 via a slot 130 through which the rod 300 bows outwardly, and a handle 200 mounted to the stylet 100 and adapted to actuate the elongate rod 300 to deform/curve the stylet 100. The endotracheal intubation device 10 can be used on a patient by a medical professional to access the patient's trachea by inserting the endotracheal tube 400 into the patient. Upon insertion, the handle 200 is actuated to deform the stylet 100.

13 Claims, 9 Drawing Sheets

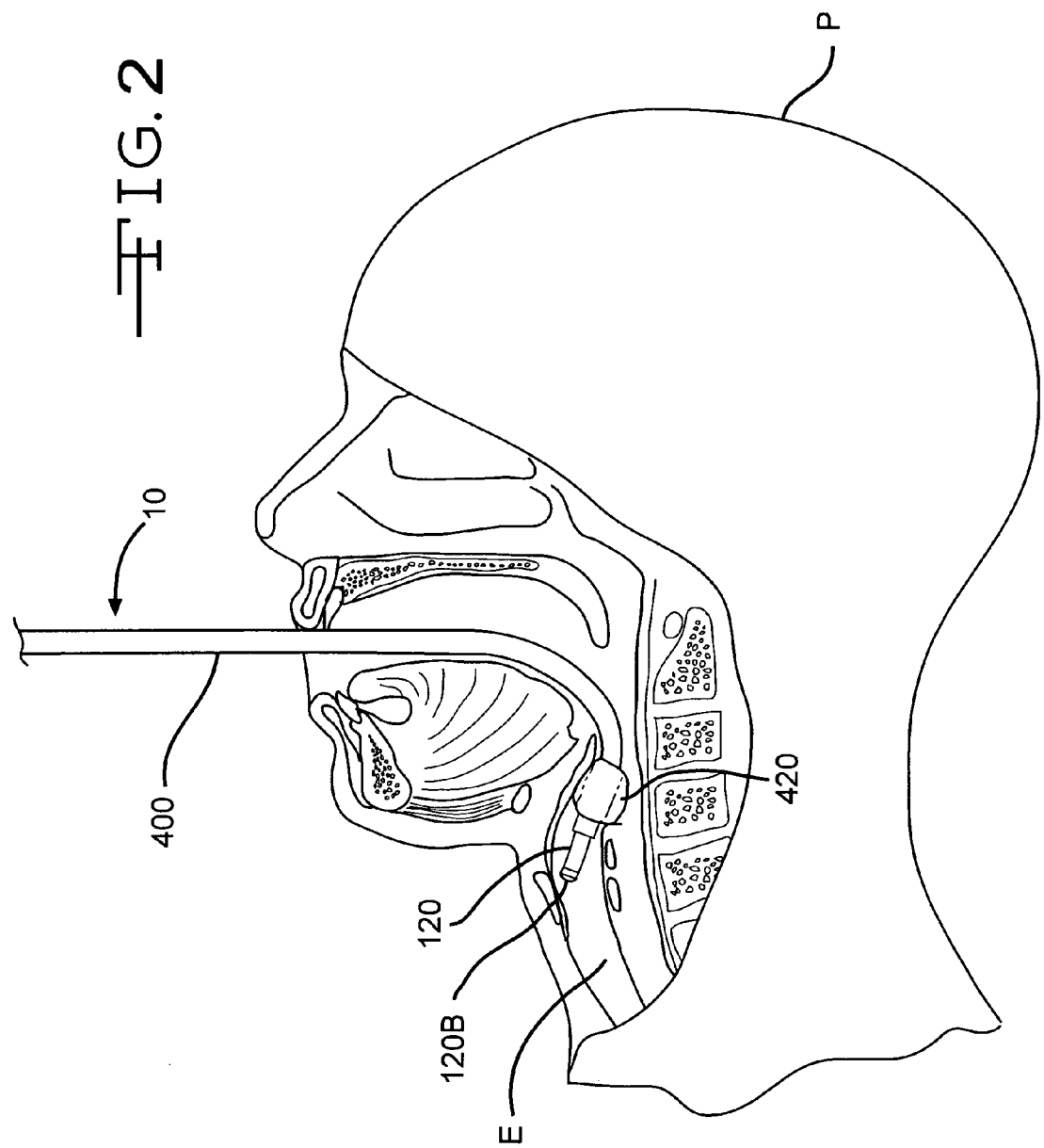

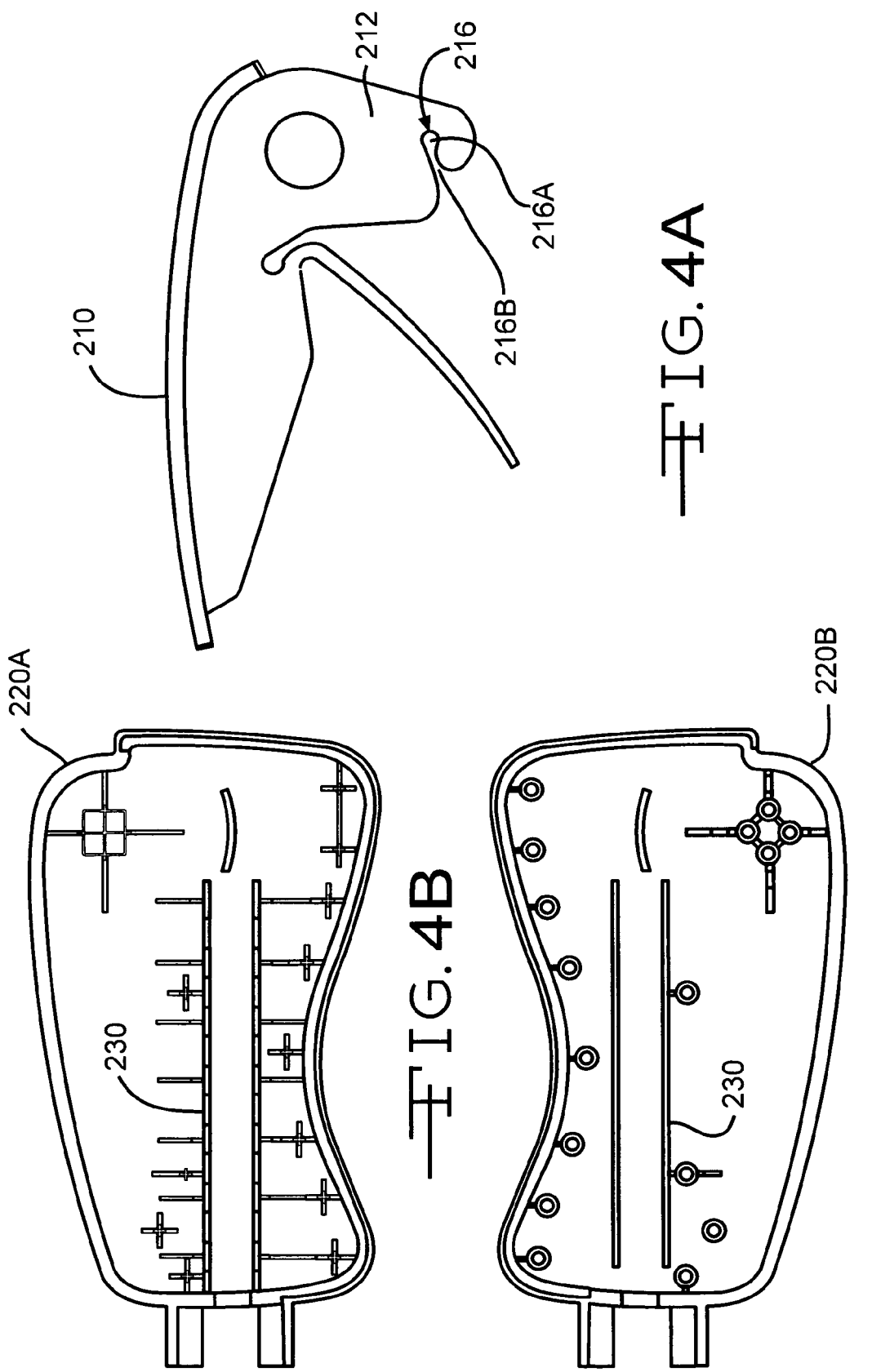

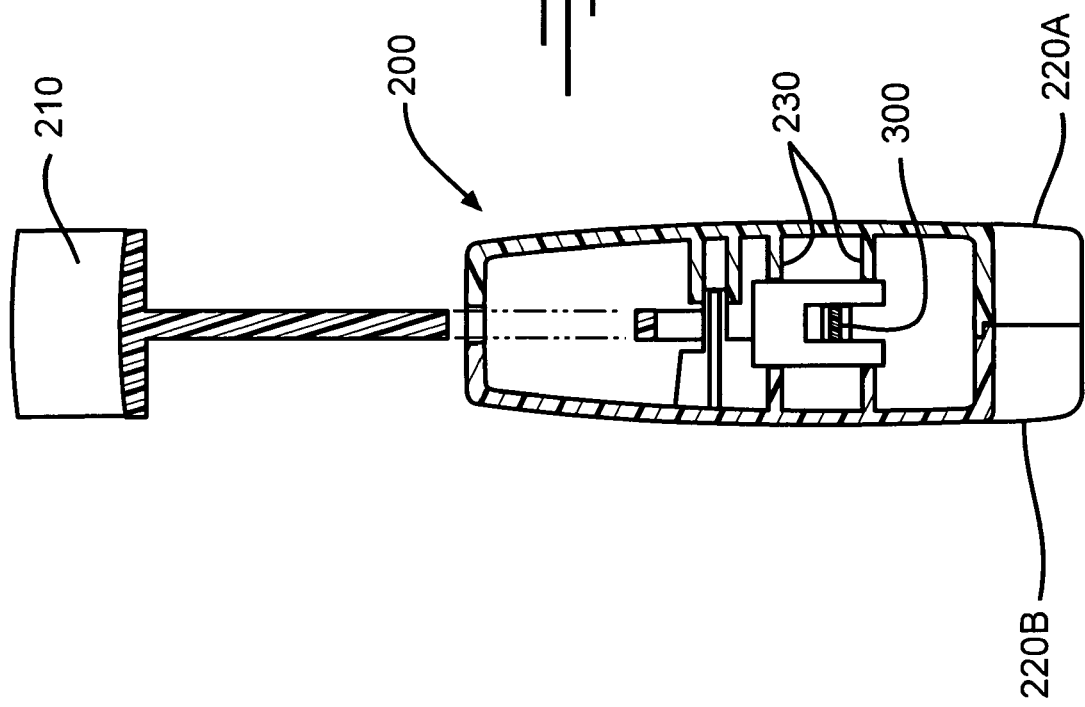

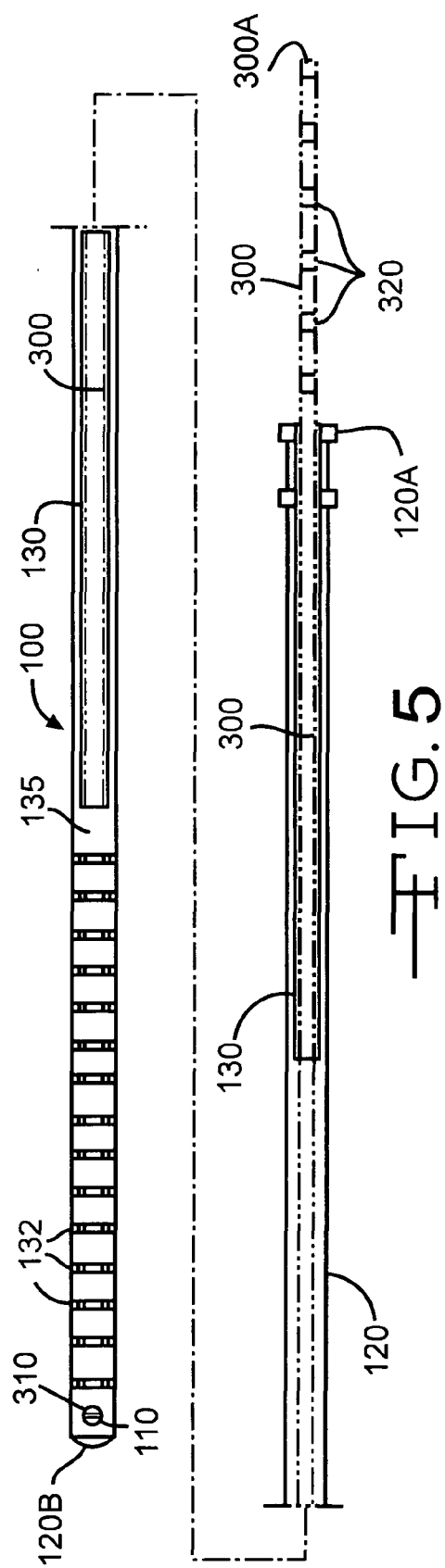
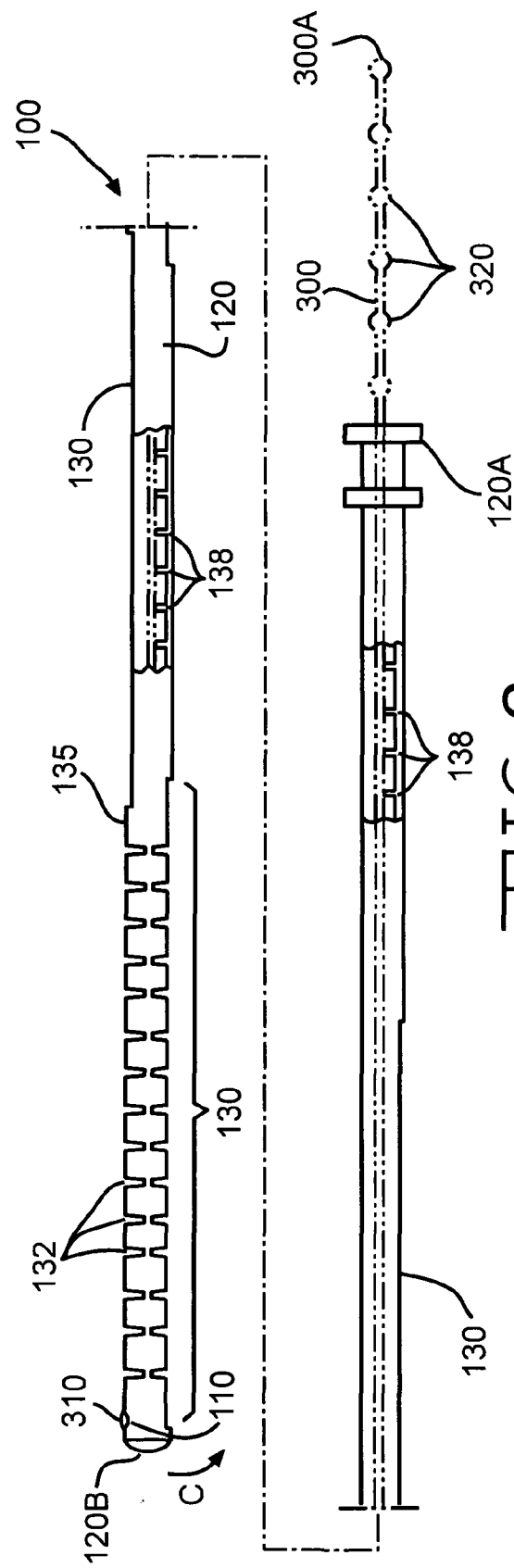
FIG. 5
FIG. 6

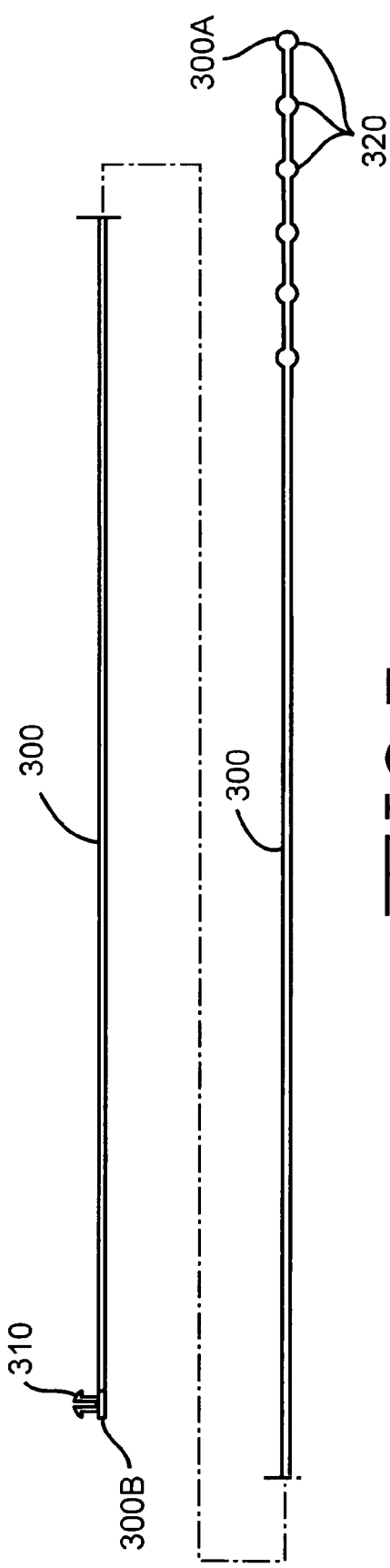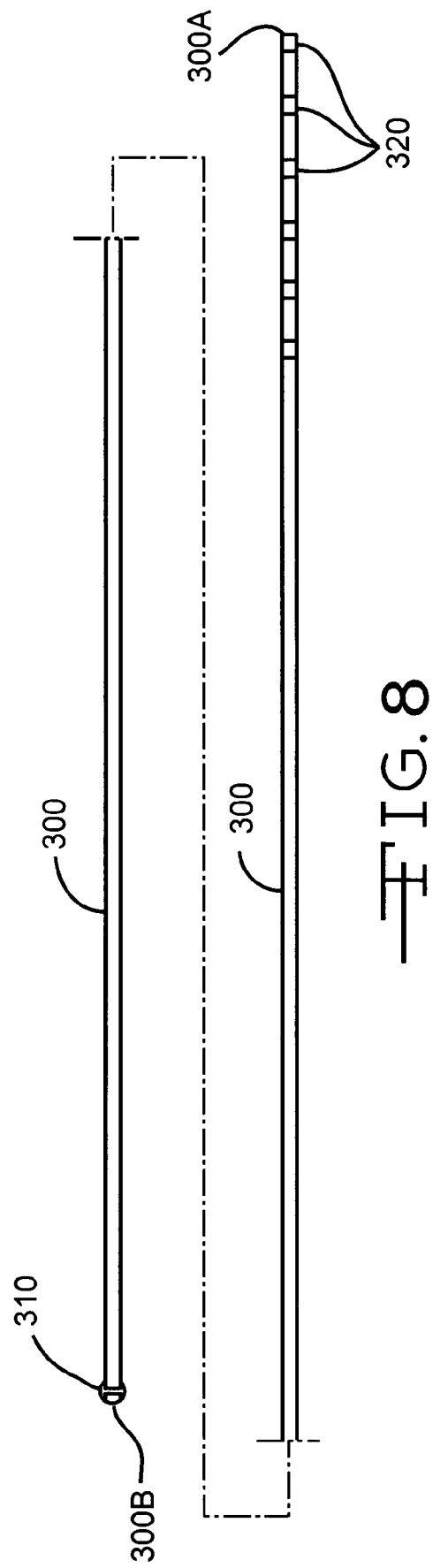

ENDOTRACHEAL INTUBATION DEVICE

CROSS-REFERENCE TO RELATED APPLICATIONS

None.

FIELD OF THE DISCLOSURE

The disclosure relates to endotracheal intubation devices, particularly to endotracheal devices having an improved means for curving the distal end of an endotracheal tube inserted into a patient.

BRIEF DESCRIPTION OF RELATED TECHNOLOGY

U.S. Pat. No. 2,975,785 to Sheldon discloses an optical viewing instrument comprising an endoscope sheath and a plurality of tube elements arranged in an end to end relationship. One end of the sheath is secured to a control housing and has its interior end in communication with the interior chamber of the housing. The control housing serves to support various control structures for the endoscope including cables which are secured to a terminal tube element with the other ends of the cables secured and looped around a pair of pulleys positioned within the chamber. The pulleys are turned by control knobs to flex a terminal section of the endoscope. The instrument has an optical system with a flexible bundle of optically aligned transparent glass fibers. The transparent glass fibers transmit light from an object which is illuminated by a pair of lamps in the end of the instrument so that an image of the object can be seen at an eyepiece.

U.S. patents issued to Bazinet (U.S. Pat. No. 3,162,214), Takahashi et al. (U.S. Pat. No. 4,236,509) and Petruzzi (U.S. Pat. No. 4,669,172) disclose flexible tubular structures composed of coiled wire and/or tethered circular ring elements which provide for flexibility in tubular structures. Petruzzi discloses a method for fabricating a flexible shaft comprising a spiral cut member having an essentially uniform inside diameter and a tapered linear profile.

U.S. Pat. No. 4,846,153 issued to Berci discloses an intubating video endoscope which includes an elongated sheath member with a selectively controllable bendable section housing an image forming optical system. A generally rigid section includes a control housing. An image transmitting optical system extends throughout the length of the sheath member and terminates adjacent to the image forming system. A light transmitting system also extends throughout the length of the sheath member to the image forming optical system, the rearward end of which is adapted to be operatively connected to a light source.

U.S. Pat. No. 4,949,716 issued to Chenoweth discloses a hand held medical device with a wide range of nasally placed airway tubes to afford better control of airway tubes. A soft flexible tube surrounding a flat spring has a braided wire which is pulled to control the flexing of the airway tube.

U.S. Pat. No. 6,539,942 to Schwartz et al., describes an endotracheal intubation device having a series of interlinked, truncated ring-like elements disposed along the distal portion of the tube and a handgrip for controlling the degree of bend in the distal end of the device. An imaging device, such as a nasopharyngoscope, can be inserted through the intubation device to visualize the patient's vocal cords during the intubation procedure. The endotracheal intubation device uses a scissors mechanism without pulleys to bend the distal end of the device.

U.S. Pat. No. 4,905,666 to Fukuda, U.S. Pat. No. 5,520,222 to Chikama and JP 5,329,095 to Ogino teach bending devices which use pulleys or chain driven winding mechanisms which are controlled by cranks and knobs.

U.S. Patent Application 2006/0004258 to Sun et al. discloses an image-type intubation-aiding device comprising a small-size image sensor and a light source module both placed into an endotracheal tube to help doctors with quick intubation. Light from light emission devices in the light source module passes through a transparent housing and is reflected by a target and then focused. The optical signal is converted into a digital or analog electric signal by the image sensor for displaying on a display device after processing. Doctors can thus be helped to quickly find the position of trachea, keep an appropriate distance from a patient for reducing the possibility of infection, and lower the medical treatment cost. Disposable products are available to avoid the problem of infection. The intubation-aiding device can be used as an electronic surgical image examination instrument for penetration into a body. Moreover, a light source with tunable wavelengths can be used to increase the spot ratio of nidus.

U.S. Patent Application 2007/0162095 to Kimmel et al. discloses visualization stylets and methods of use, in which the visualization stylets include modular components that allow interchangeability of imaging devices and lenses, and the use of forward-facing or lateral-facing lens orientations. Optionally, the lens may be focused remotely. A reduced insertion profile is provided by configuring the circuitry of the imaging device so that it is disposed substantially perpendicular to a plane of a pixel array of the imaging device.

SUMMARY

The disclosure relates to endotracheal intubation device comprising: (a) a stylet comprising an elongate, hollow tube with a slot in a wall along a longitudinal axis of the tube adjacent a distal end wherein the device is adapted to mount an endotracheal tube for intubating a patient; (b) an elongate rod (e.g., being substantially flat or having a flat portion) mounted inside the hollow tube along the axis and attached to the hollow tube at the distal end so that a portion of the rod is exposed in the slot in the tube; and (c) a handle mounting the stylet at a proximal end of the rod with an actuating means (e.g., a trigger to which the rod is directly connected) mounted on the handle's housing enabling movement of the rod along the longitudinal axis, wherein when the actuating means moves the rod in the hollow tube, the distal end of the tube curves along the slot so that the rod bows out of the slot enabling movement against an interior surface of the endotracheal tube as the distal end of the tube curves.

Various refinements of the endotracheal intubation device are possible. For example, the device can be constructed as a single-use, disposable device (e.g., such that any or all of its components are formed from a disposable plastic material). Additionally, the elongate rod at its proximal end can have one or more balls/ribs/cylinders which snap fit into a slot in a pivot arm of the actuating means (or trigger). The handle housing can comprise a pair of shells which snap fit together. A length of the hollow tube and the elongate rod can be adjustable to provide various lengths of endotracheal tube by shortening the tube and a removable segment of the rod which is provided with multiple spaced apart connections enabling the actuating means. In an embodiment, a digital camera and a light are mounted at the distal end of the hollow tube enabling viewing of the airway of a patient and wherein the camera is in communication with a screen which enables viewing of the airway during intubation.

The disclosure also relates to a method of intubating a patient, the method comprising: (a) providing an endotracheal intubation device according to any of the various disclosed embodiments, the device further comprising an endotracheal tube mounted on the stylet of the device; (b) inserting the sytlet and the endotracheal tube into the trachea of the patient; (c) actuating the handle of the device to deform (e.g., curve) the stylet and conform the shape of the endotracheal tube to the shape of the patient's tracheal passageways; (d) removing the stylet from the patient and leaving the endotracheal tube in the patient's trachea, thereby intubating the patient; and optionally (e) disposing of the endotracheal intubation device after a single use. Prior to insertion of the stylet, the length of the stylet and the elongate rod can be adjusted (e.g., shortened to a length appropriate for the patient).

The following U.S. patents and patent applications are incorporated by reference herein in their entireties for all purposes: Ser. No. 11/230,392 (filed Sep. 29, 2005), Ser. No. 11/514,486 (filed Sep. 1, 2006; now U.S. Pat. No. 7,458,375), Ser. No. 11/820,117 (filed Jun. 18, 2007), Ser. No. 11/906,870 (filed Oct. 4, 2007), Ser. No. 12/148,033 (filed Apr. 16, 2008), Ser. No. 12/148,050 (filed Apr. 16, 2008), and Ser. No. 12/587,905 (filed Oct. 15, 2009). In general, the structure, construction, and methods for the endotracheal intubation devices disclosed herein can be incorporated into the endotracheal intubation devices of the foregoing patents/patent applications.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples, drawings, and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein:

FIG. 2 is a front view of a human head in partial section showing the placement of the endotracheal tube in the airway of a patient using the device of FIGS. 1 and 1A.

FIGS. 4A, 4B, 4C, are 4D are drawings of the separated internal parts of the handle and the trigger of FIG. 3.

FIGS. 5 and 6 are front views (top and side, respectively) of the stylet which together show the positioning of the rod in dotted lines.

FIGS. 7 and 8 are views of the rod in front and plan view.

Figure 1:
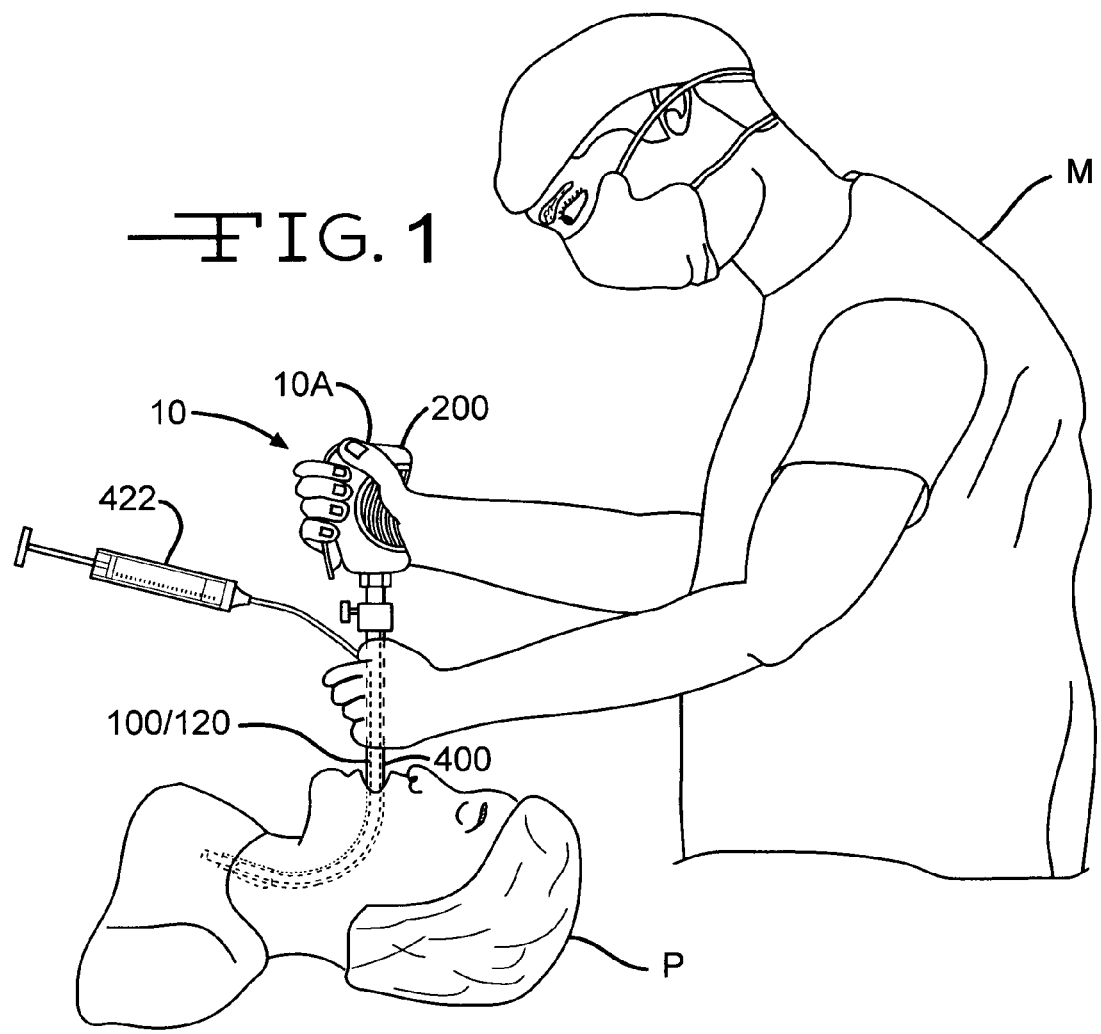
FIG. 1 is a front view of one embodiment of an endotracheal intubation device wherein the distal end on the patient's airway has an improved means for curving the tip of the stylet as shown in FIG. 1A.

While the disclosed apparatus and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

With reference to FIGS. 1-10, the present disclosure generally relates to a preferred endotracheal intubation device 10 including a stylet 100, an elongate rod 300 mounted within the stylet 100 and adapted to deform/curve the stylet 100 as well as to have an endotracheal tube 400 mounted thereto, and a handle 200 mounted to the stylet 100 and adapted to actuate the elongate rod 300 to deform/curve the stylet 100. In an embodiment, the endotracheal intubation device 10 is intended as a disposable, single-use device (e.g., with its components variously formed from disposable plastic materials).

FIGS. 1 and 2 illustrate the endotracheal intubation device 10 in use on a patient P. The device 10 is operated by a medical professional M to access the patient P's trachea E by inserting the endotracheal tube 400 that is mounted onto the stylet 100 (e.g., around the outer surface of the stylet 100) into the patient P via the mouth. Upon insertion, the handle 200 is actuated to deform the stylet 100 and allow insertion of the stylet 100 and the endotracheal tube 400 through curved passageways in the trachea E of the patient P. The endotracheal tube 400 is constructed from a generally flexible material so that it can deform along with the stylet 100 when the handle 200 is actuated and maintain a shape that conforms to the tracheal passageways of the patient P upon removal of the intubation device 10. The illustrated device 10 further includes a balloon 420 (e.g., inflatable with a plunger 422) positioned around the endotracheal tube 400 at or near the distal end 120B of the hollow tube 120.

Figure 10:
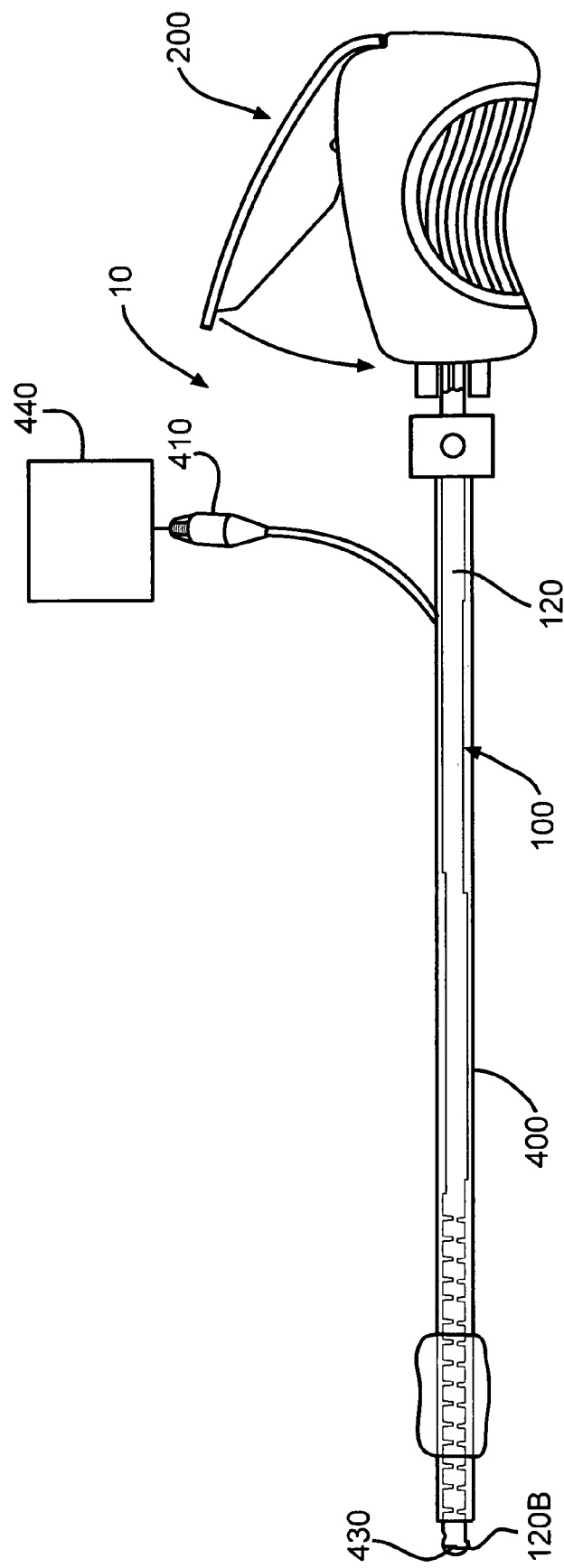

As shown in FIG. 10, the endotracheal intubation device 10 can further include a digital camera (e.g., CCD, CMOS) and/or a light source (e.g., LED) that are collectively illustrated as element 430 attached to the device 10 (e.g., mounted at or near the distal end 120B of the hollow tube 120). The camera and light are connected by a cable 410 (e.g., extending through the hollow tube 120) to a video screen 440 (e.g., in electronic communication with a computer and monitor) to enable the viewing of the airway of patient P during intubation.

Stylet

Figure 1A:
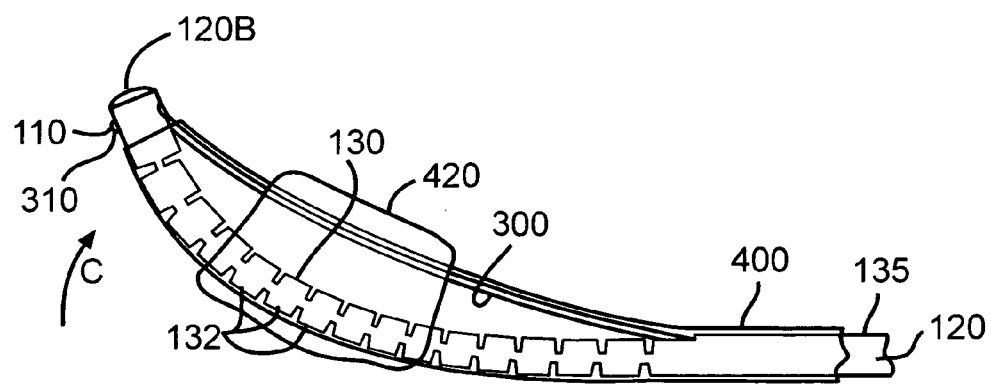

As more particularly shown in FIGS. 1A, 5, and 6, the stylet 100 generally includes an elongate, hollow tube 120 (e.g., formed from a disposable plastic material) having (i) a proximal end 120A for mounting (e.g., detachably or permanently) the stylet 100 to the handle 200 and (ii) a distal end 120B for insertion into the trachea E of the patient P. When the hollow tube 120 is in a generally straight, non-deformed configuration, the tube 120 defines a longitudinal axis A-A (FIG. 9) between its proximal and distal ends 120A, 120B. The hollow tube 120 includes a slot 130 in a wall 135 of the tube 120. The slot 130 generally extends in a direction along the longitudinal axis A-A, suitably in a portion of the wall 135 that is adjacent (i.e., at or near) the distal end 120B of the hollow tube 120. In the illustrated embodiment, the hollow tube 120 includes three slots 130: one slot 130 on the top side of the tube 120 and two slots 130 on the bottom side of the tube 120. The three slots 130 are generally located at alternating positions along the longitudinal axis A-A. As shown in FIG. 1A, it is the left-most slot 130 of FIG. 6 through which the elongate rod 300 outwardly bows upon actuation of the actuating means 210. As further illustrated, an internal surface of the wall 135 in the hollow tube 120 can include a plurality of ribs/spacers 138 along at least a portion of the tube 120 length. The ribs/spacers 138 help to maintain the elongate rod 300 generally positioned along the axis A-A in the regions of the hollow tube 120 where the tube 120 is not deformed (i.e., generally straight). The hollow tube 120 also includes an opening 110 at or near the distal end 120B of the hollow tube 120 to facilitate attachment/mounting of the elongate rod 300 to the tube 120.

As illustrated, the hollow tube 120 can include a corrugated/ribbed portion 132, also suitably located adjacent the distal end 120B of the hollow tube 120. The ribbed portion 132 generally includes alternating sections (i) having a diameter/height substantially equal to that of the other portions of the hollow tube 120 and (ii) having a diameter/height substantially smaller than that of the other portions of the hollow tube 120. The alternating large and small diameters/heights permit the hollow tube 120 to deform upon actuation of the handle 200 and elongate rod 300. In the illustrated embodiment, the width of the hollow tube 120 remains substantially constant notwithstanding the variable height of the tube 120 along its length, thus constraining the hollow tube 120 (and stylet 100) to curve within a plane and substantially in one direction (i.e., curvature toward the side of the tube 120 where the slot 130 and the opening 110 are located).

Elongate Rod

Figure 3:
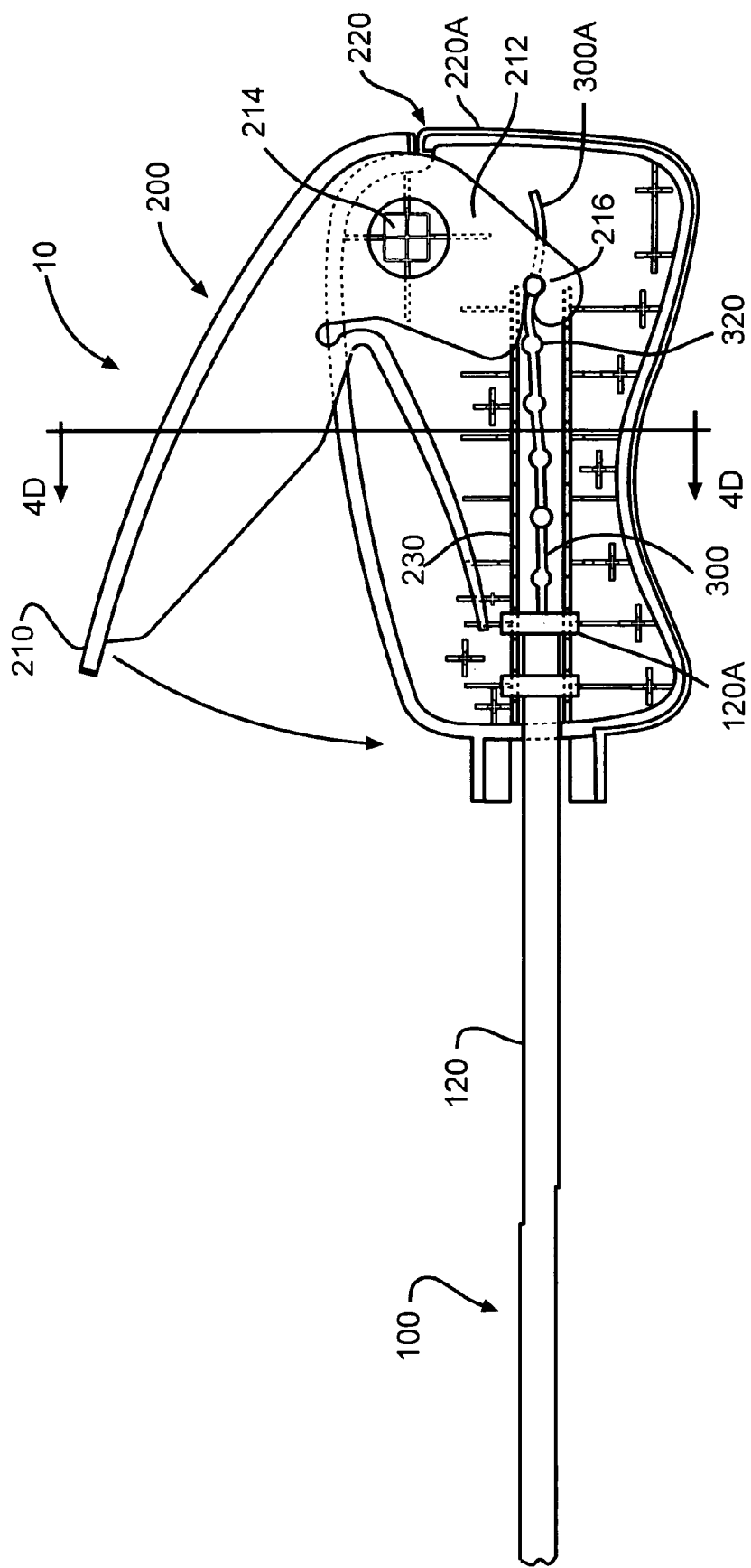
FIG. 3 is a longitudinal cross-sectional view of an embodiment of the handle of the endotracheal device showing a trigger and the rod enabling curving of the distal tip of the stylet.
Figure 9:
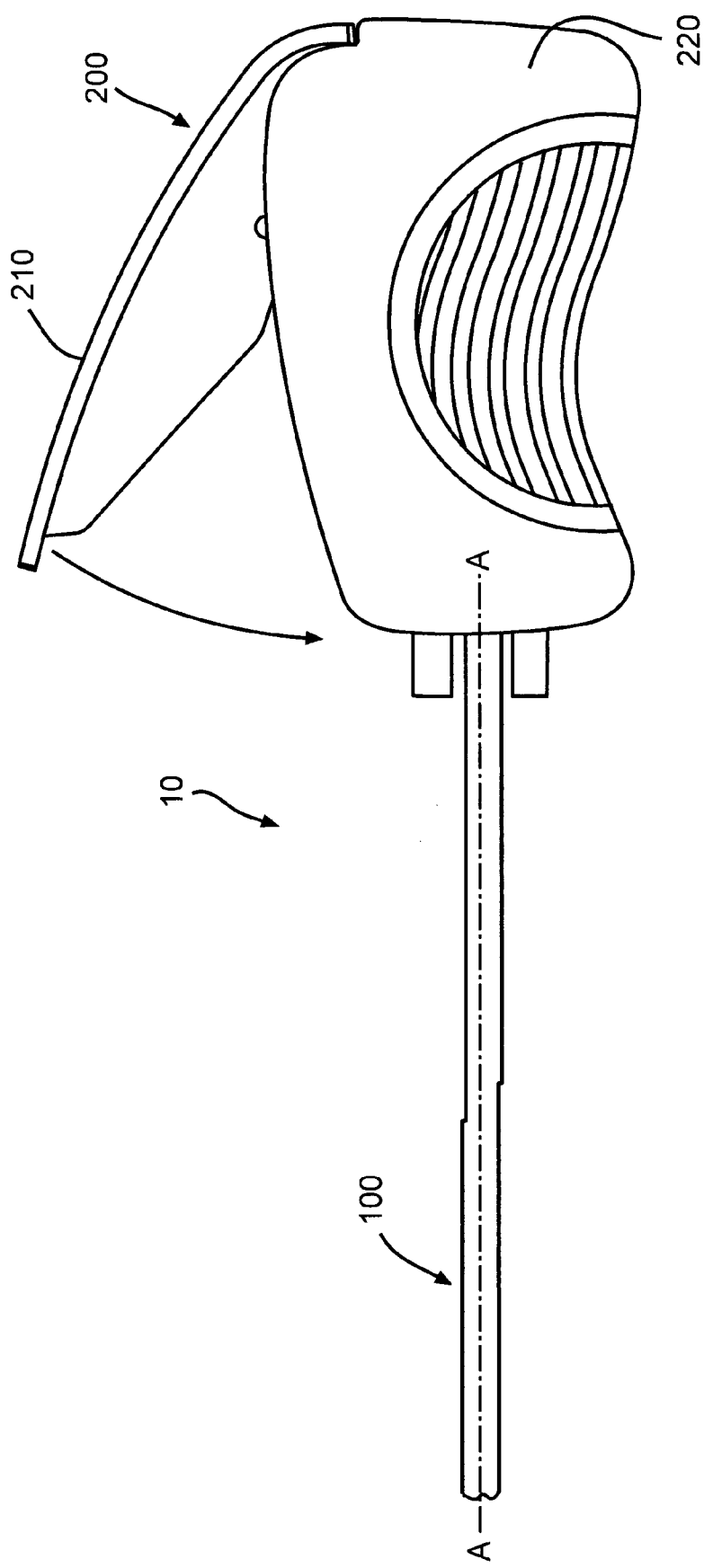
FIGS. 9 and 10 are side views which together show the assembled endotracheal intubation device.

As more particularly shown in FIGS. 3, 7, and 8, the elongate rod 300 has a substantially flat, flexible, elongate construction (e.g., formed from a flexible, disposable plastic material such as a nylon material in a tape-like configuration) extending between a proximal end 300A and a distal end 300B. In other embodiments (not shown), the rod 300 can have other shapes/construction (e.g., string or wire shape, metal or polymeric material, substantially cylindrical shaped, substantially circular cross section, substantially flexible construction along entire length or in regions intended for curvature/deformation, partially rigid construction in regions not intended for curvature). The elongate rod 300 includes a pin 310 (or other attachment means) at the distal end 300B for mounting the rod 300 to the hollow tube 120 (e.g., a snap-fit connection between the pin 310 and the opening 110 in the tube 120). The elongate rod 300 further includes a ball/rib 320 (or other attachment means) at the proximal end 300A for attaching the rod 300 to an actuating portion of the handle 200.

As illustrated, the elongate rod 300 includes a plurality of balls/ribs 320, thus allowing the length of the endotracheal intubation device 10 to be adjusted prior to use (i.e., depending on the length of the endotracheal tube 400 that would be appropriate for the size of a particular patient P). Specifically, the elongate rod 300 can be shorter/shortened such that at least one ball/rib 320 remains for attachment to the handle 200 (e.g., to a trigger 210 as described in more detail below). Similarly, the length of the stylet 100 can be adjusted/shortened, for example (i) by forming the hollow tube 120 from a plurality of interconnecting sections, one or more of which can be removed prior to use, or (ii) by providing a plurality of tubes 120 of varying lengths (e.g., in a kit also containing one or more handles 200 and elongate rods 300, where the rods 300 also could have varying lengths corresponding to those of the plurality of tubes 120).

Handle

As more particularly shown in FIGS. 3 and 4A-4D, the handle 200 generally includes a housing 220 that, in the illustrated embodiment, includes two half-shell portions 220A and 220B (e.g., formed from a rigid, disposable plastic material) that snap-fit together. The handle 200/housing 220 provides a central structure for integration/mounting of the device 10 components, including the stylet 100, the elongate rod 300, and an actuating means 210 (e.g., a trigger means). The actuating means 210 enables movement of the elongate rod 300 along the longitudinal axis A-A (e.g., in a direction toward the proximal end 10A of the device 10 when the actuating means 210 is actuated/depressed/pulled/etc.). As illustrated, the actuating means 210 is a trigger 210 that is depressed to move the elongate rod 300 along the longitudinal axis A-A. The housing 220 includes a pair of internal walls 230 that define a channel for mounting the stylet 100 at the proximal end 120A of the hollow tube 120 inside the housing 220.

The trigger 210 is mounted to a rotation axis 214 (i.e., a pivot point), thus allowing the trigger 210 to rotate and to cause movement of the elongate rod 300 upon depression of the trigger 210. In the illustrated embodiment, the actuating means 210 includes a pivot arm 212 that rotates on/around the rotation axis 214 upon depression of the trigger 210. The pivot (or lever) arm 212 includes a gripping portion 216 that fixedly holds the ball/rib 320 (or other attachment structure) on the elongate rod 300, thus causing the elongate rod 300 to move as the pivot arm 212 rotates. As more particularly illustrated in FIG. 4A, the gripping portion 216 has a semi-circular cross-section/opening 216A with a diameter that generally corresponds to (e.g., slightly larger than) the diameter of the ball/rib 320 (e.g., which can have a generally spherical or cylindrical shape). The gripping portion 216 further includes a slot 216B having height a gap that is narrower than the height/diameter of the ball/rib 320 and the generally corresponds to (e.g., slightly larger than) the thickness of the elongate rod 300. This configuration allows the proximal end 300A of the elongate rod 300 to be threaded and/or secured into the gripping portion 216 (e.g., in a snap-fit configuration).

The mechanical connections at the proximal and distal ends 300A, 300B of the elongate rod 300 enable movement of the elongate rod 300, resulting in the deformation/curvature of the stylet 100/hollow tube 120, in particular at the distal end 120B of the tube 120. Tension applied to the elongate rod 300 by movement of the actuating means 210 moves/slides the elongate rod 300 in the hollow tube 120, thereby causing the distal end 120B of the tube 120 to curve along the slot 130 so that the rod 300 bows out of the slot 130 and rides upwardly against the inside surface of the endotracheal tube 400 (e.g., as illustrated in FIG. 1A). This direction of deformation/curvature upon application of tension is shown in FIGS. 1A and 6 by arrow C. Conversely, release of tension can relax the elongate rod 300 to a substantially straight configuration.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clarity of understanding only, and no unnecessary limitations should be understood therefrom, as modifications within the scope of the disclosure may be apparent to those having ordinary skill in the art.

Throughout the specification, where the compositions, processes, apparatus, or systems are described as including components, steps, or materials, it is contemplated that the compositions, processes, or apparatus can also comprise, consist essentially of, or consist of, any combination of the recited components or materials, unless described otherwise. Component concentrations expressed as a percent are weight-percent (% w/w), unless otherwise noted. Numerical values and ranges can represent the value/range as stated or an approximate value/range (e.g., modified by the term "about"). Combinations of components are contemplated to include homogeneous and/or heterogeneous mixtures, as would be understood by a person of ordinary skill in the art in view of the foregoing disclosure.

What is claimed is:

1. An endotracheal intubation device comprising:
   (a) a stylet comprising an elongate, hollow tube with a slot in a wall along a longitudinal axis of the elongate, hollow tube adjacent a distal end wherein the device is adapted to mount an endotracheal tube for intubating a patient;
   (b) an elongate rod mounted inside the elongate, hollow tube along the axis and attached to the elongate, hollow tube at the distal end so that a portion disposed between a proximal and a distal end of the rod is exposed in the slot in the elongate, hollow tube; and
   (c) a handle housing mounting the stylet at a proximal end of the rod with an actuating means mounted on the housing enabling movement of the rod along the longitudinal axis, wherein when the actuating means moves the rod in the elongate, hollow tube, the distal end of the elongate, hollow tube curves along the slot so that the rod bows out of the slot enabling movement against an interior surface of the endotracheal elongate, hollow tube as the distal end of the tube curves.

2. The device of claim 1 adapted for a single use.

3. The device of claim 1 or 2, wherein a portion of the rod along the slot is flat.

4. The device of claim 1 or 2, wherein the rod connects directly to a trigger as the actuating means mounted in the housing.

5. The device of claim 1 or 2, wherein the rod at the proximal end has a ball which snap fits into a slot in a pivot arm of the actuating means.

6. The device of claim 1 or 2, wherein the housing comprises a pair of shells which snap fit together.

7. The device of claim 1 or 2, wherein a digital camera and a light are mounted at the distal end of the elongate, hollow tube enabling viewing of the airway of a patient and wherein the camera is in communication with a screen which enables viewing of the airway during intubation.

8. The device of claim 1 or 2, wherein the elongate, hollow tube and end are made of a disposable plastic material.

9. The device of claim 1 or 2, wherein a length of the elongate, hollow tube and rod are adjustable to provide various lengths of endotracheal tube by shortening the elongate, hollow tube and a removable segment of the rod which is provided with multiple spaced apart connections enabling the actuating means.

10. The device of claim 1 or 2, wherein the actuating means is a trigger.

11. A method of intubating a patient, the method comprising:
    (a) providing the endotracheal intubation device of claim 1, the device further comprising an endotracheal tube mounted on the stylet of the device;
    (b) inserting the sytlet and the endotracheal tube into the trachea of the patient;
    (c) actuating the handle of the device to deform the stylet and conform the shape of the endotracheal tube to the shape of the patient's tracheal passageways; and
    (d) removing the stylet from the patient and leaving the endotracheal tube in the patient's trachea, thereby intubating the patient.

12. The method of claim 11, further comprising:
    (e) disposing of the endotracheal intubation device after a single use.

13. The method of claim 11, further comprising: prior to insertion of the stylet, adjusting the length of the stylet and the elongate rod.

* * * * *